United States Patent [19]

Holland et al.

[11] Patent Number: 5,685,307

[45] Date of Patent: Nov. 11, 1997

[54] METHOD AND APPARATUS FOR TISSUE CHARACTERIZATION OF ANIMALS USING ULTRASOUND

[75] Inventors: Kyle H. Holland, Lincoln, Nebr.; David L. Carlson, Ames, Iowa

[73] Assignee: Iowa State University Research Foundation, Inc., Ames, Iowa

[21] Appl. No.: 395,844

[22] Filed: Feb. 28, 1995

[51] Int. Cl.$^6$ ...................................................... A61B 8/00
[52] U.S. Cl. .............................. 128/660.01; 128/661.03
[58] Field of Search ........................ 128/660.01, 660.06, 128/660.07, 661.01, 661.03, 662.03

[56] References Cited

U.S. PATENT DOCUMENTS

| | | |
|---|---|---|
| 4,106,346 | 8/1978 | Matzuk . |
| 4,344,159 | 8/1982 | Ballinger ........................ 128/662.03 X |
| 4,359,056 | 11/1982 | Carlson . |
| 4,553,437 | 11/1985 | Luthra et al. . |
| 4,603,702 | 8/1986 | Hwang et al. ..................... 128/660.01 |
| 4,785,817 | 11/1988 | Stouffer . |
| 4,901,729 | 2/1990 | Saitoh et al. ..................... 128/662.03 |
| 5,140,988 | 8/1992 | Stouffer et al. . |
| 5,398,290 | 3/1995 | Brethour ........................ 128/660.01 X |
| 5,415,167 | 5/1995 | Wilk ............................. 128/903 X |

Primary Examiner—Francis Jaworski
Attorney, Agent, or Firm—Henderson & Sturm

[57] ABSTRACT

A method and apparatus for tissue characterization of animals using ultrasound wherein the apparatus generally comprises a hand-held ultrasound transducer array, a power source, a data acquisition unit and a communications means for coupling the hand-held ultrasound transducer array to the data acquisition unit. Display means and input means are provided for the control of the device by a user. The method includes gathering data concerning the animal tissue by using the apparatus to generate and receive ultrasound signals into and from the animal tissue and then processing the data which are gathered. This processing includes analyses which determine whether or not the hand-held ultrasound transducer array was positioned correctly relative to the animal tissue as well as the fat percentage and marbleization of the tissue.

8 Claims, 5 Drawing Sheets

METHOD AND APPARATUS FOR TISSUE CHARACTERIZATION OF ANIMALS USING ULTRASOUND

TECHNICAL FIELD

This invention relates to using ultrasound technology for purposes of characterizing the tissue of a carcass animal wherein such characterization includes fat percentage and marbleization.

BACKGROUND ART

With the rise of ultrasound technology in the medical field in recent years, many uses for such technology have found their way into other industries. One industry which has found particular use for ultrasound is that of meat processing.

Currently, the grading of meat is carried out by inspectors who are specially trained to rate animal carcasses on the basis of visual inspection. This system is inherently subjective and potentially unfair due to the variability of human judgement, especially from inspector to inspector. Furthermore, the present grading system requires that the carcasses be at least partially butchered in order for grading to take place. This process is prone to rendering all or a portion of the carcass under analysis unusable. This baseline waste is currently taken for granted. Still further, the process of grading by human inspectors takes significant time due to the aforementioned butchering and visual inspection. This is undesirable for two reasons. First, the longer the carcass is exposed to the environment, the more it deteriorates due to natural processes and the higher the potential for external contaminants, such as dust and bacteria, adversely affecting carcass quality. These all, of course, constitute potential health hazards. Secondly, the number of carcasses a plant can process contributes directly to the plant's profits. Wasted time is costly.

Therefore, a method for the grading of meat in an automatic, efficient, non-invasive, and, most importantly, objective manner has long existed. Much progress has been made in the use of ultrasound technology to address this need; however, the method in which this progress has taken form have proven to be deficient in that they are somewhat costly and unnecessarily complicated or are not capable of determining particular characteristics of animal carcass tissue which it may be desirable to know.

A probable cause for these deficiencies is the fact that ultrasound technology has been developed furthest in the medical field where it is often used to generate images of internal tissue. U.S. Pat. Nos. 4,785,817 and 5,140,988 both by Stouffer (et al in the latter) teach methods for grading meat and detecting abnormal bone structure (respectively) which lie along these lines. However, when such methods are used, especially in the grading of meat, complications arise. The generation of such images is data handling intensive, thereby necessitating considerable computing power, and also require further processing, such as pattern recognition steps, in order to arrive at a grade. The clarity of these images also raises questions as to the reliability of such techniques.

U.S. Pat. No. 4,785,817 also requires the use of brackets and arms to ensure proper and consistent positioning of its transducer array on an animal. Proper use of these positioning devices in applying them from animal is potentially time consuming. This is especially true if the animals are of considerably different size which would necessitate adjustment of these positioning devices.

Automatic determination of meat quality indicators without the use of imaging have been developed successfully. One such apparatus is taught in U.S. Pat. No. 4,359,056 by Carlson (also co-inventor in this application) which is an automatic digital backfat meter. While this device is quite capable of determining fat thickness along the back of an animal, it is incapable of determining the characteristics of lean tissue, such as fat percentage and marbleization, which are the factors used primarily in the grading of meat as described above.

Thus, those concerned with these and other problem recognize the need for an improved apparatus and method for the characterization of animal tissue using ultrasound technology.

DISCLOSURE OF THE INVENTION

The present invention includes a method and apparatus for tissue characterization of animals using ultrasound wherein the apparatus generally comprises a hand-held ultrasound transducer array, a power source, a data acquisition unit and a communications means for coupling the hand-held ultrasound transducer array to the data acquisition unit. Display means and input means are provided for the control of the device by a user. The method includes gathering data concerning the animal tissue by using the apparatus to generate and receive ultrasound signals into and from the animal tissue and then processing the data which are gathered. This processing includes analyses which determine whether or not the hand-held ultrasound transducer array was positioned correctly relative to the animal tissue as well as the fat percentage and marbleization of the tissue.

An object of the present invention is the provision of an improved method and apparatus for the characterization of animal tissue using ultrasound technology which is portable, efficient, and accurate.

Another object is to provide for the determination of specific tissue characteristics, such as fat percentage and marbleization.

A further object of the invention is the provision of means for storing data from at least one animal carcass for analysis either immediately or possibly at a later time.

Still another object is to provide a means for communicating to the user whether or not the hand-held transducer array has been properly positioned and that acceptable contact between it and the animal carcass has been made when it is applied to a particular anatomical location on the animal carcass.

A still further object of the present invention is the provision of means for allowing the user to easily control the device and handle data which are gathered.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 1:
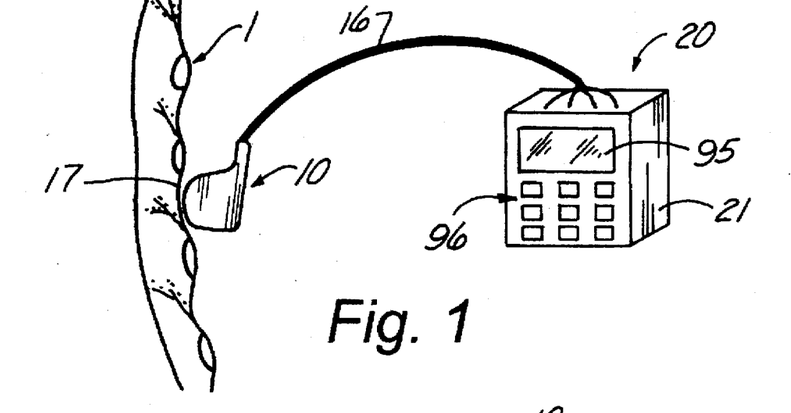
FIG. 1 is a diagrammatic view of the apparatus in its intended operating position.

Referring now to the drawings, wherein like reference numerals designate identical or corresponding parts throughout the several views, FIG. 1 shows the apparatus in its intended environment. A beef carcass (1) whose tissue is being characterized is shown here for purposes of illustration; however, it should be understood that any of a variety of carcasses of like-sized animals (e.g., hogs or sheep) could be analyzed for tissue characterization using the apparatus and method described herein with only superficial modifications. While the term "carcass" will be used hereinafter to describe the tissue being characterized, it should be made clear that the invention could conceivably be used on live animals.

Figure 12:
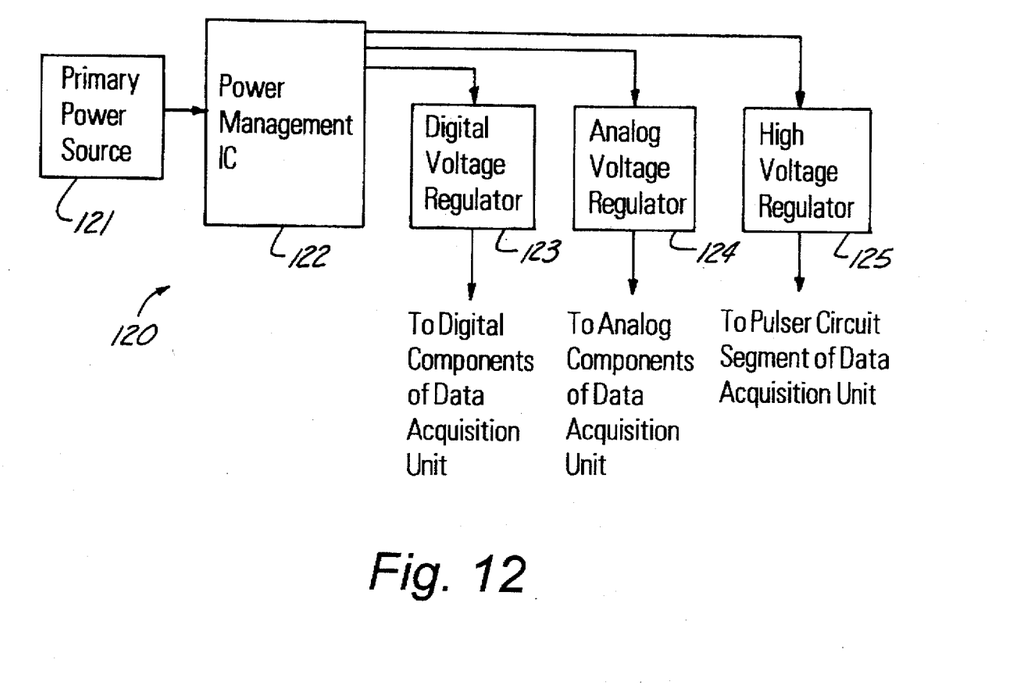
FIG. 12 is a block diagram of the organization of the power source.

The apparatus of this invention generally comprises an ultrasound transducer array (10) a size suitable to be held in the hand, a data acquisition unit (20), and a power source (120) (see FIG. 12). A complete description of these components and their functionality is given below.

Figure 2:
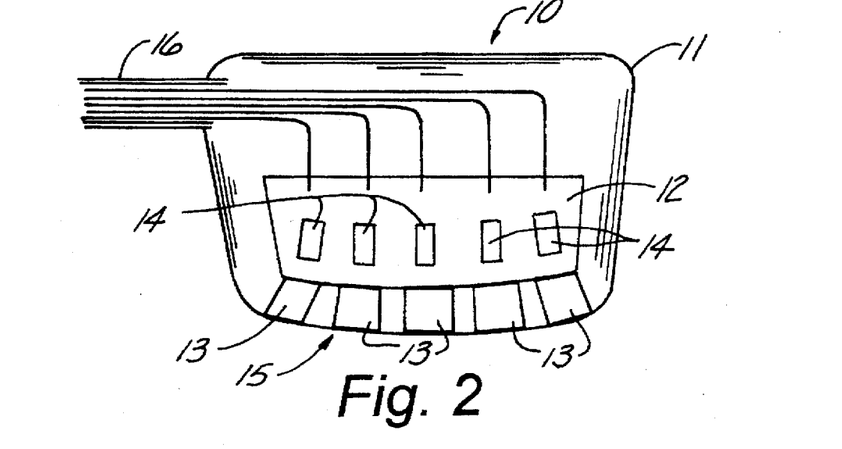
FIG. 2 is a lateral section of the hand-held ultrasound transducer array.

The transducer array (10), whose specific mode of operation will be described in more detail below, is shown in FIG. 1 in the operating position preferred by the present invention. Referring now to FIG. 2, the hand-held transducer array (10) comprises a housing (11), an imbedded mounting structure (12), a plurality of transducer elements (13), a plurality of tuning inductances (14) equal in number to the plurality of transducer elements (13), a tissue contact surface (15), and a communications means (16).

The housing (11) is of a size and shape suitable to be easily held in the hand of a typical user without undue fatigue. Further, the housing (11) is constructed of a moldable substance, such as a plastic or epoxy, such that the remainder of the elements of the hand-held transducer array (10) may be imbedded within it, thereby providing these elements with structural support, protection against mechanical stress (e.g., being dropped), and protection against fluids, such as blood or water, which are common in a meat-processing environment.

Within the housing (11), a generally flat, rectangular imbedded mounting structure (12) is provided for the purpose of giving structural support to the tuning inductances (14) or any other necessary electronic components, such as those needed to isonify, amplify, record, or otherwise process data or signals which are collected with respect to the carcass (1). In the preferred embodiment, the imbedded mounting structure (12) is a printed circuit board which further allows electrical connections to be easily made between the transducer elements (13), the tuning inductances (14), and the communications means (16).

Figure 3:
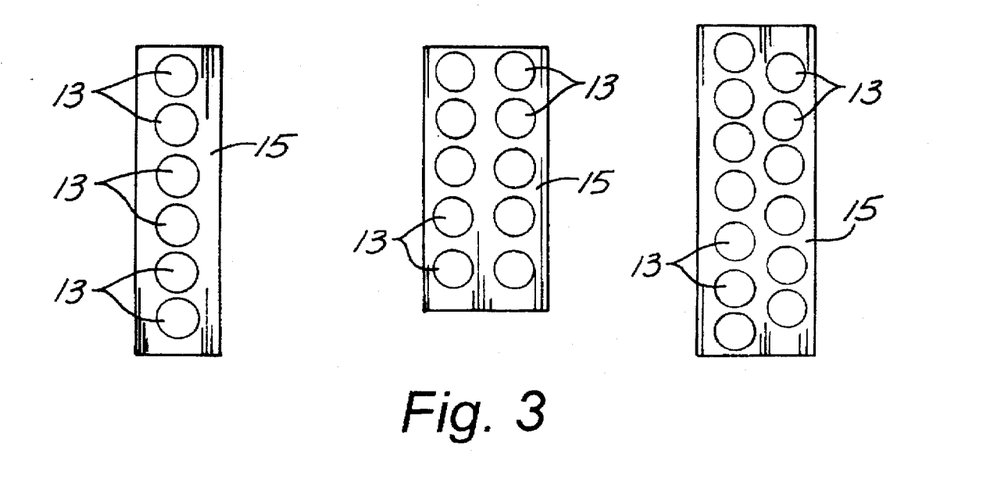
FIG. 3 is a plan view of the tissue contact surface of the hand-held transducer array in several forms.

Along the edge of the imbedded mounting structure (12) proximal to the tissue contact surface (15), a plurality of transducer elements (13) are arranged in a predetermined pattern. Referring now to FIG. 3, which is a plan view of the tissue contact surface (15), it is seen that this pattern may take any of a multitude of forms such as linear (FIG. 3a), matrix (FIG. 3b), or cluster (FIG. 3c). It should of course be understood that FIG. 3 serves to illustrate only a few of many possible arrangements.

Figure 4:
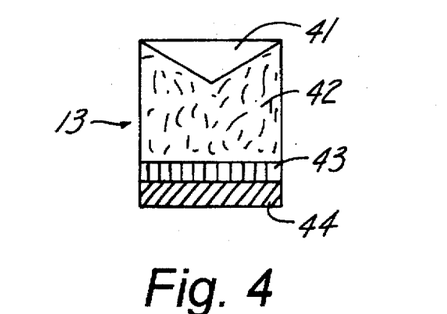
FIG. 4 is a diagrammatic side view of a piezo-electric transducer element in an upright position.
Figure 5:
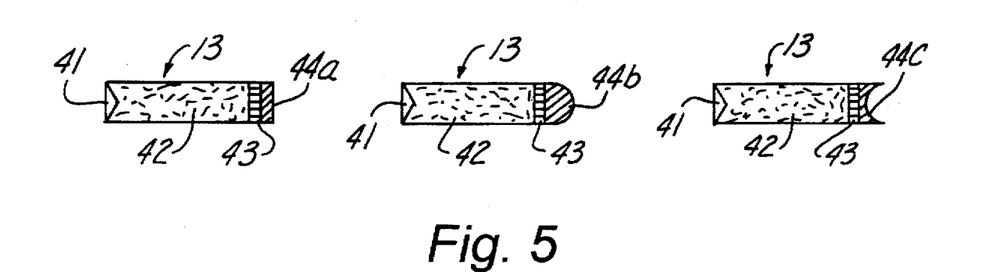
FIG. 5 is a diagrammatic side view of a piezo-electric transducer element in a sideways position with variable matching layer configurations.

Referring to FIG. 4, which is a diagrammatic view of a single transducer element (13), each transducer element (13) comprises a conical indentation (41), a backing layer (42), a piezo-electric element (43), and a matching layer (44). Such transducer elements are well known in the art. The matching layer (44) is of a particular thickness which is determined as follows. It is known in the art that optimal transmission and reception of an ultrasound signal is achieved when the matching layer thickness is a quarter wavelength of the sound wave as it propagates through the matching layer (44); and, when the material from which the matching layer (44) is made is of an acoustic impedance equal to the geometric mean of the two materials being matched (in this case, the piezo-electric element (43) and the tissue being characterized (1)). Furthermore, the matching layers (44) may be any of several shapes. Referring to FIG. 5, it is shown that these shapes may be generally flat, i.e., unfocused (44a); convex, i.e., defocused (44b); or concave, i.e., focused (44c). These options are shown in FIGS. 5a, 5b, and 5c respectively. The shapes of the matching layers (44) provide a means for controlling the scattering of ultrasound signals as they are transmitted into the tissue being characterized (1). For example, a concave matching layer (44c) directs ultrasound signals to a particular depth within the tissue, i.e., focuses the ultrasound signals, while a convex matching layer (44b) directs the signals in a scattered way into the tissue, i.e., defocuses the ultrasound signals.

Figure 6:
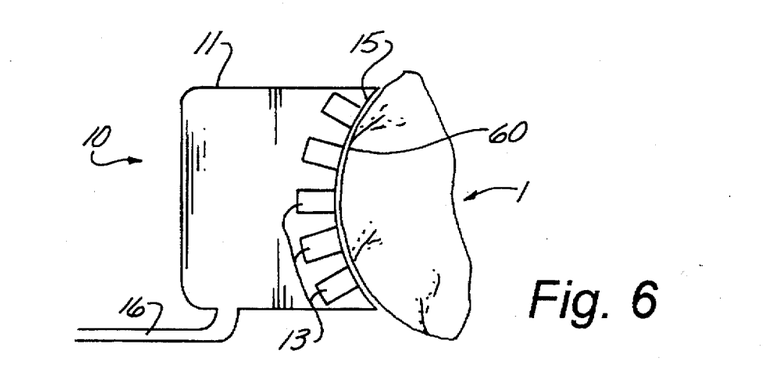
FIG. 6 is a diagrammatic view of the hand-held ultrasound transducer array with a flexible tissue contact surface in contact with an irregular tissue surface.

Returning now to FIGS. 2 and 4, the matching layer (44) of each of the transducer elements (13) is disposed outwardly relative to the interior of the housing (11) so as to form an integral part of the tissue contact surface (15). In one embodiment, the tissue contact surface (15) is constructed from a rigid substance and is of a generally outwardly arcuate shape so as to conform to a carcass tissue surface which is of a complementary shape, for example, the area between two adjacent ribs (17). In another embodiment, as illustrated in FIG. 6, the tissue contact surface (15) is constructed from a flexible material so as to allow the transducer array (10) to make matching contact with a carcass tissue surface which is of a somewhat irregular or convex shape (60). In either of these embodiments, the constructions of the tissue contact surface (15) allows for the formation of contact between the matching layers (44) of the transducer elements (13) and the tissue of a carcass (1) that is of sufficient quality for the transmission and reception of ultrasound signals.

Figure 7:
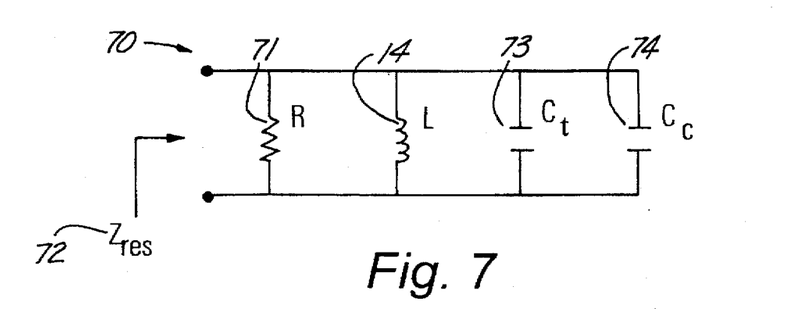
FIG. 7 is a schematic of an equivalent model for a transducer element and other associated elements.

Again referring to FIG. 2, associated with each transducer element (13) is one of a plurality of tuning inductances (14). The tuning inductances (14) are mounted upon the imbedded mounting structure (12), within the housing (11), intermediate to the transducer elements (13) and the communications means (16). Each of the tuning inductances (14) is at one end electrically coupled to an associated transducer element (13) and at the other end electrically coupled to the communications means (16). The purpose of the tuning inductances is brought to light with reference to FIG. 7 which is an equivalent model (70) of an operating transducer element (13). Here R represents the dampening resistance (71) of the transducer element (13). It is known in the art that the maximum electrical and acoustic sensitivity for a transducer occurs when it is operated at resonance. That is to say when the capacitive and inductive elements (i.e., the reactive elements) of a transducer are of values such that the impedance, $Z_{res}$ (72), as seen from outside the model, is purely resistive, the transducer is operating at maximal electric and acoustic sensitivity. It is well known in the art that such a situation arises when the reactance of the inductive elements of the model equals the reactance of the capacitive elements of the model. Mathematically, that is $$X_L = X_C \qquad \text{(Eq. 1)}$$

$$\omega L = \frac{1}{\omega C}$$

Where L is the tuning inductance (14), C is the sum of the transducer capacitance $C_t$ (73) and the cable capacitance $C_c$ (74), and ω is the thickness-mode resonance frequency (in rads/sec) of the piezo-electric element (43) of the transducer element (13). By substituting the fact that ω=2πf, where f is the thickness-mode frequency (in Hertz) of the piezo-electric element (43), and solving for L, we arrive at the equation used to design for the tuning inductances of the present invention:

$$L = \frac{1}{\omega^2 C} = \frac{1}{4\pi^2 f^2 C} \qquad \text{(Eq. 2)}$$

Figure 8:
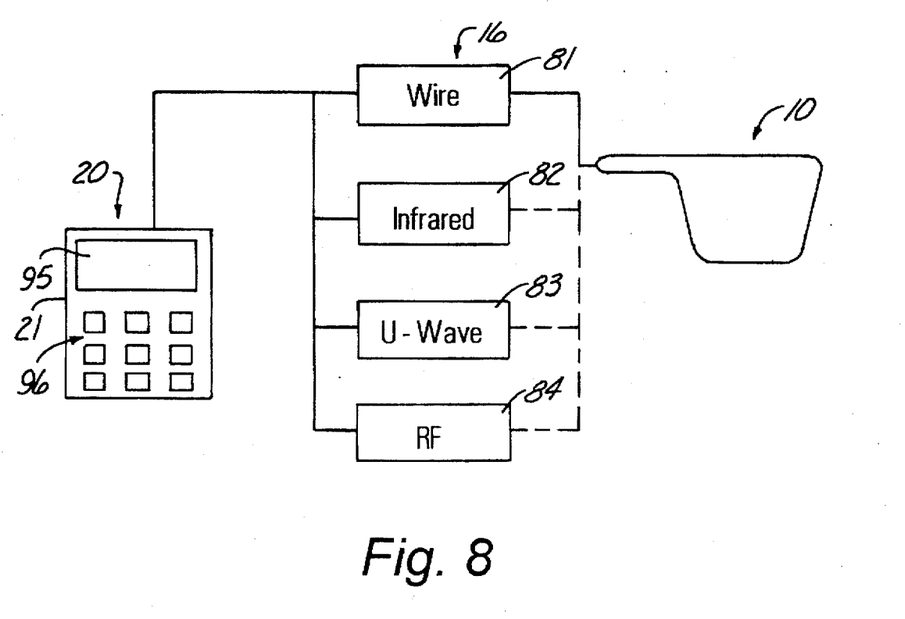
FIG. 8 is a diagrammatic representation of optional means for communication between the data acquisition unit and the hand-held ultrasound transducer array.

The transducer array (10) is operably coupled by communications means (16), for example one or more cables, to the dam acquisition unit (20). The communication means (16) is at one end electrically connected to the plurality of tuning inductances (14) and at the other end electrically connected to elements of the data acquisition unit (20) which will be described in more detail below. It should also be understood that any of a number of communications means (16) could be employed. FIG. 8 illustrates only a few possibilities for this purpose. For example, there are many well known wireless technologies that could easily be used by one skilled in the art to accomplish this task. Such technologies include but are not limited to infrared (82), microwave (83), and radio frequency (RF) (84). The use of wire (81) is also shown as a communication means (16).

Returning to FIG. 1, the data acquisition unit (20) is contained within a housing (21) which is constructed of a durable material such as shock-resistant plastic or metal. The size and shape of the housing (21) is such that the data acquisition unit (20) may be held in the hand of a typical user.

Figure 9:
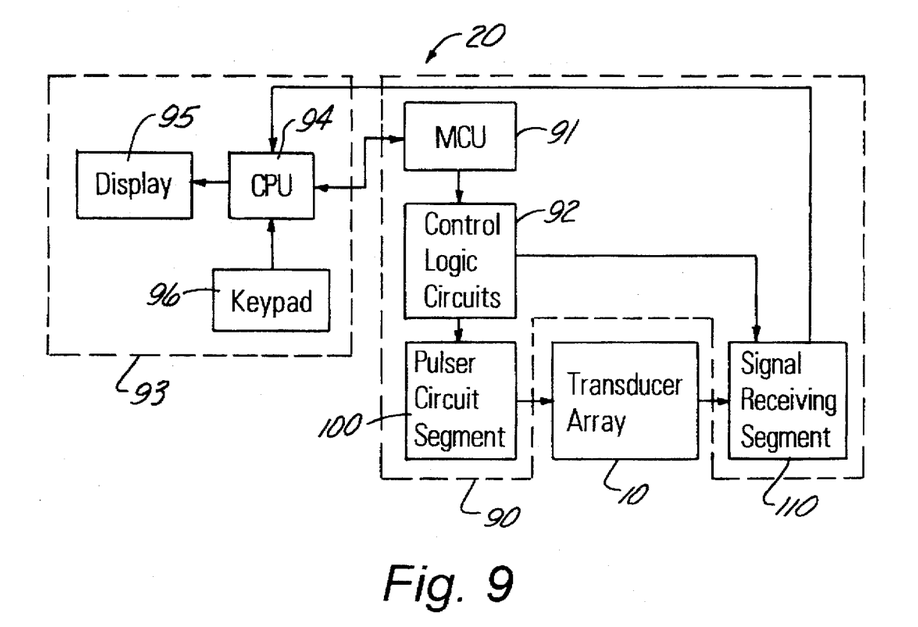
FIG. 9 is a block diagram of the internal architecture of the data acquisition unit in association with the hand-held ultrasound transducer array.

Turning now to FIG. 9, which is a block diagram of the data acquisition unit, the data acquisition unit (20) comprises both an ultrasound signal processing portion (90) and a user interface portion (93). Generally, the purpose of the ultrasound signal processing portion (90) is to generate, send, receive, and record in a useful way, ultrasound signals. The user interface portion (93) provides a means for the user of the apparatus to control the way in which such signals are processed and further to handle data which are gathered. The operation of these portions will now be described in detail.

The ultrasound signal processing portion (90) comprises a microcontroller unit (MCU) (91), a control logic circuit segment (92), a pulser circuit segment (100), and a signal receiving segment (110).

The MCU (91) is responsible for the control of the ultrasound signal processing portion (90). Many of the elements within the remainder of the ultrasound signal processing portion (90) have control characteristics which are not directly compatible with the MCU (91). Therefore control logic circuits (92) are provided. The control logic circuits (92) receive instructions from the MCU (91) in a particular binary format and then control their respective elements of the ultrasound signal processing potion (90) in a predetermined way which carries out the instructions of the MCU (91). With this in mind, any references hereinafter to actions of the MCU (91) carried out in conjunction with other elements of the ultrasound signal processing portion (90) shall be understood to have been carried out via the control logic circuits (92).

Figure 10:
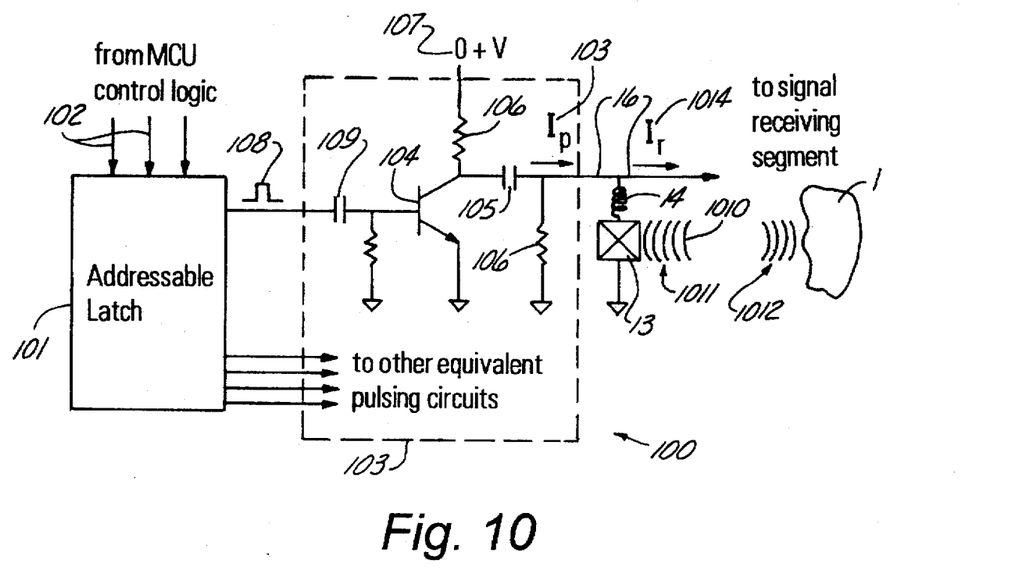
FIG. 10 is a schematic view of the pulser circuit segment.

A detail of the pulser circuit segment (100) is illustrated schematically in FIG. 10. An addressable latch (101) is provided which allows the MCU (91) to select, via control lines (102), one of a plurality of equivalent pulsing circuits (103). Each pulsing circuit (103) is operably coupled to an individual transducer element (13) via the communication means (16). For the sake of simplicity, only one of these pulsing circuits (103) is shown.

The main components of the pulsing circuit (103) are a switching transistor (104) and a pulsing capacitor (105). Resistors (106) are also provided for purposes of biasing the switching transistor (104). A coupling capacitor (109) is provided as well. When the pulsing circuit (103) is not being used, the switching transistor (104) is not conducting current. This causes the charging voltage (107) to bring the pulsing capacitor (105) to an equal voltage. That is to say the pulsing capacitor (105) becomes charged. When the MCU (91) selects the pulser circuit (103) from among the other equivalent pulsing circuits (103) and subsequently sends a pulse signal (108), the switching transistor (104) of the selected pulsing circuit (103) conducts electric current, and the pulsing capacitor (105) discharges causing a pulsing current $I_p$ (1013) to stimulate the transducer element (13). The piezo-electric element (43) of the transducer element (13) mechanically deforms as a result of this electrical stimulation and an ultrasound wave (1010) results. Repeated stimulation of the transducer elements (13) causes a series of ultrasound waves (1010) to be produced thereby creating an outgoing ultrasound signal (1011). As the transducer elements (13) are arranged within the housing (11) of the transducer array (10) as previously described, the outgoing ultrasound signals (1011) are readily directed into the carcass (1). The transducer elements (13) are intended to be brought into direct contact with the carcass (1); however, a separation is shown in FIG. 10 for clarity of illustration.

The reflected ultrasound signal (1012) returning from the carcass (1) is detected by the transducer element (13). This detection is in the form of a mechanical deformation of the piezo-electric element (43) of the transducer element (13) which results in an electric signal $I_r$ (1014) which is representative of the strength of the mechanical deformation and thus the strength of the reflected ultrasound signal (1012). $I_r$ (1014) is passed on, via communication means (16), to the signal receiving segment (110) of the ultrasound signal processing portion (90) of the data acquisition unit (20).

Figure 11:
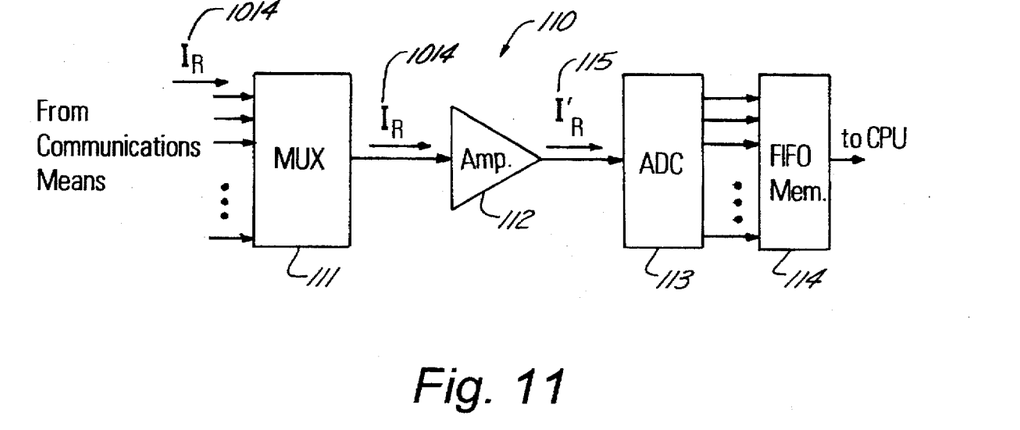
FIG. 11 is a schematic view of the signal receiving segment.

Referring now to FIG. 11, which is a block diagram detail, the signal receiving segment (110) comprises a multiplexer (MUX) (111), an amplifier (112), an analog to digital converter (ADC) (113), and a first-in-first-out (FIFO) memory (114).

The MUX (111) serves as the counterpart to the addressable latch (101) of the pulser circuit segment (100). That is to say electric signals, $I_r$ (1014), which are representative of reflected ultrasound signals (1012) received by individual transducer elements (13) are singly routed from the communications means (16) through the MUX (111) by the MCU (91) to the remaining elements of the signal receiving segment (110).

As each electrical signal $I_r$ (1014) is routed through the MUX (111), it is passed to an amplifier (112). The amplifier (112) serves to increase the amplitude of the electric signal $I_r$ (1014) in order to create an amplified electric signal $I_r'$ (115). The amplifier (112) is capable of two modes of amplification, high and low, whose functions will be described below.

The amplified electric signal $I_r'$ (115) is subsequently passed from the amplifier (112) to the ADC (113). Here the amplified electric signal $I_r'$ (115) is subjected to conversion into a digital form which is suitable for electronic storage. This digital form is a series of binary numbers which have magnitudes representative of the amplitude of the amplified electrical signal $I_r'$ (115) at serial points in time.

The binary numbers are stored in the FIFO memory (114) as they are generated by the ADC (113). The FIFO memory (114) is capable of storing a predetermined number of binary numbers and is generally filled to or near its capacity before its contents are passed on to other portions of the apparatus for analysis as will be described below.

In a given scan of a particular carcass (1), the MCU (91) will, in turn, cause each transducer element (13) to generate outgoing ultrasound signals (1011) and then digitize and record the corresponding reflected ultrasound signals (1012) in the manner described immediately above. It should be made clear that the pattern of creation of outgoing ultrasound signals (1011) and recordation of reflected ultrasound signals (1012) in the use of the present invention as described immediately above is unimportant so long as the pattern does not create more signals than can be stored by the FIFO memory (114) and the MCU (91) controls the pattern in a known way. For example, the outgoing ultrasound signals (1011) created by the transducer elements (13) may be of the same frequency or of different, individual frequencies or some combination thereof.

Returning now to FIG. 9, the user interface portion (93) of the data acquisition unit (20) comprises a central processing unit (CPU) (94), a keypad (96), and a display (95). The display (95) is preferably of a compact, light-weight construction, such as that provided by the use of liquid crystal technology. The general physical appearance of these elements can be seen in FIG. 1 and FIG. 8.

The CPU (94), keypad (96), and display (95), constitute a hand-held micro-computer. The main operating program of this hand-held microcomputer resides in the memory of the CPU (94) and provides both a user interface program and a data analysis program. The user interface program will be discussed first. The data analysis program is an integral part of the method for tissue characterization and will be described in a later portion of this description.

In the preferred embodiment, the user interface program is "menu driven" meaning that the user is visually provided with a list of options (or "menu") by way of the display (95) from which to choose. These options include various actions which the user may take with respect to the use of the device. For example, some options are concerned with the device per se such as control of the contrast of the display (95) or the status of the power supply (120). Other options are for purposes of initiating an ultrasound scan of a carcass (1). Still other options provide a means for the initiation of analysis, transfer, or deletion of gathered data. These options are selected and executed by the user through the use of the keypad (96).

FIG. 12 is a block diagram of the power source (120) of the present invention. The power source (120) is contained within the housing (21) of the data acquisition unit (20) and generally comprises a primary power source (121), a power management IC (122), a digital voltage regulator (123), an analog voltage regulator (124), and a high voltage regulator (125).

The primary power source (121) is typically a battery (or several batteries) which provides direct current to the power management IC (122). The use of battery power in the present invention allows for increased portability of the apparatus as compared, for example, to the use of conventional alternating current (AC) which would necessitate a power cord. However, a particular user might deem the advantage of virtually uninterrupted use of the present invention through conventional AC power more valuable than the portability afforded by battery power which, of course, requires occasional recharging or replacement of the battery. In this case, one skilled in the art could easily provide modifications to the apparatus which would allow AC power to be the primary power source (121).

The power management IC (122) is capable of producing both positive and negative voltages of varying amplitudes. Thus the power management IC (122) is a primary voltage regulator. The power management IC (122) is also capable of monitoring the voltage of the primary power source (121) and passing this information on to the CPU (94) of the data acquisition unit (20). The CPU can then, via the display (95), keep the user appraised of, for example, low battery voltage.

Once the power management IC (122) has performed the primary voltage regulation, voltages of various amplitudes and polarity are available for regulation to very specific levels as required by the various components of the data acquisition unit (20). The digital voltage regulator (123) is a circuit which provides at its output the specific voltage needed for the proper operation of the digital components (e.g., the MCU (91) and control logic segment (92)) whereas the analog voltage regulator (124) provides the voltages necessary for the analog components (e.g., the amplifier (112) of the signal receiving segment (110)). The high voltage regulator (125) provides the charging voltage (107) of the pulsing circuit segment (100). See FIGS. 9, 10, and 11.

Once ultrasound scans of one or more carcasses (1) have been made, the FIFO memory (114) may download its data, which are representative of the results of the one or more scans, to a data analysis program (attached as Appendix 1). For purposes of this discussion, this data analysis program will be understood to be part of the main operating program which resides in the memory of the CPU (94) as described above. However, it should be made clear that the data analysis program could reside in an external location, such as another computer. Such an arrangement would allow the external computer to perform the analysis on gathered data while the apparatus could be used to perform scans on other carcasses (1). Means for downloading the FIFO memory (114) to an external computer could easily be provided by one skilled in the art.

The data analysis program has two functions. First, it provides a method for ascertaining whether or not the transducer array (10) is in a proper position and has made contact with the carcass (1) of sufficient quality to allow clear transmission and reception of ultrasound signals as described above. Generally this is such that the longitudinal axes of the transducer elements (13) are approximately perpendicular to the tissue surface of the carcass (1). Second, the data analysis program characterizes certain qualities of the carcass (1), namely fat percentage and marbleization, based upon the results of an acceptable scan. The methods for accomplishing these tasks will now be described.

Figure 13:
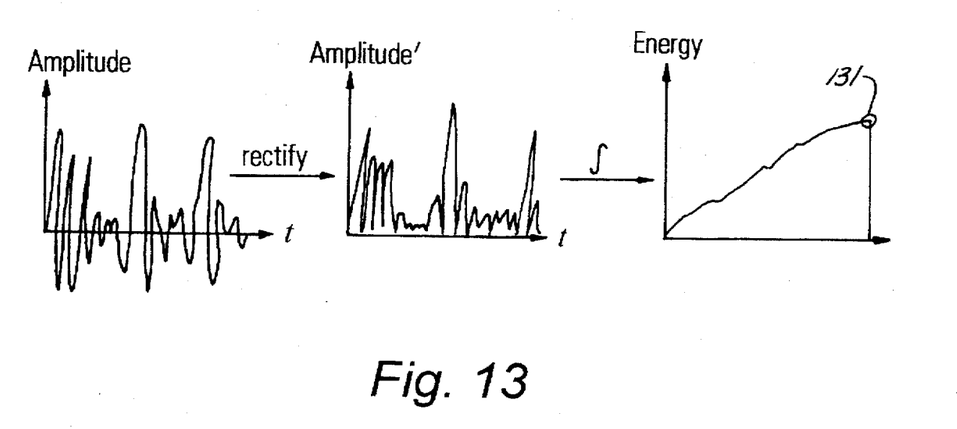
FIG. 13 is a graphical representation of the analysis process to which raw data is subjected.

References to FIG. 13 will be included in the discussion that follows. FIG. 13a is representation of the data gathered in a scan of a particular carcass (1). This graph is the result of the binary data stored in the FIFO memory (114) being filtered and plotted by the data analysis program. The next step the data analysis program takes is to rectify this waveform thus creating the plot represented by 13b. Once rectified, the signal is integrated mathematically to give an indication of the energy of the reflected ultrasound signal (1012) as is represented by FIG. 13c.

In order to ascertain that good contact has been made, the apparatus first uses the amplifier (112) in high mode to check the energy level (131) of a reflected ultrasound signal (1012) from an anatomical landmark, such as the far wall of the carcass (1). High energy reflections indicate good positioning and contact of the transducer array (10) with respect to the carcass (1) whereas low energy reflections indicate poor contact or positioning. The data analysis program compares the energy level (131) of a particular reflected ultrasound signal (1012) to a predetermined threshold level and a determination of either good or poor transducer array position and contact quality is made. If the position and contact quality is determined to be poor, the user is directed, via the display (95), to reposition the transducer array (10) and initiate a new ultrasound scan.

If the position and contact quality is good, a second scan is made using the amplifier (112) in low mode. This signal is then analyzed in a way similar to that used to ascertain position and contact quality of the transducer array (10). That is, the signal is first digitized, filtered, and rectified. However, an average of this rectified signal over the time of the scan is subsequently taken. The result of this averaging is a dimensionless quantity which is termed "energy index (EI)". The EI is then used to characterize the qualities of the carcass (1) mentioned above. Generally, the higher the EI, the higher the fat percentage; likewise, the higher the EI, the higher the marbleization. When properly calibrated, the apparatus gives particular values for these characteristics to the user via the display (95).

Thus, it can be seen that at least all of the stated objectives have been achieved.

Obviously, many modifications and variations of the present invention are possible in light of the above teachings. It is therefore to be understood that, within the scope of the appended claims, the invention may be practiced otherwise than as specifically described.

Appendix 1

DATA ANALYSIS PROGRAM LISTING

```
/*************************************************************
TITLE:          Data Analysis Program
WRITTEN BY:     Kyle Holland
DATE:           6/93
DEPARTMENT:     Dept. of Biomedical Engineering DESCRIPTION: The purpose of this program is to extract an individual
carcass sample out of the binary file uploaded from the TI-78 and
determine the backscatter energy content of each transducer. In addition,
the gain type is selected via the keyboard. The data file contains two set
of data with separate gains, 40 dB or 60 dB.
*************************************************************/
#include <stdio.h>
#include <math.h>
#include <stdlib.h>
```

Appendix 1-continued

DATA ANALYSIS PROGRAM LISTING

```
#include <string.h>
#include <process.h>
#include <conio.h>
#include <graph.h>
#include <io.h>
#include <sys\types.h>
#include <sys\stat.h>
include <fcntl.h> char gain, sptr, num[20];
signed char g;
static unsigned char c, dbuf[2048], usrecord[6][2048];

int topblk, i, j, x, y, z, sreg[6];
long rec_num, sum[6], sum123, sum456, sum1to6;

FILE *fptr;

main( )
{
    _clearscreen(_GCLEARSCREEN);
    _setvideomode(_VRES2COLOR);
    _setcolor(1);
    do
    {
        do
        {
            _clearscreen(_GCLEARSCREEN);
            printf("Enter record number(1–15)");
            gets(num);
            rec_num = atol(num);
            printf("%d \n",rec_num);
        }
        while((rec_num > 15) || (rec_num < 1));
        printf("Is Above Information Correct?(y, n or ESC to quit)");
        c = getch( );
    }
    while((c == 'N') || (c == 'n') || (c == 0x0d));
    if (c == 0x1b)
        exit(1);
    do
    {
        do
        {
            _clearscreen(_GCLEARSCREEN);
            printf("High gain? <Enter y or n> \n");
            gain = getch( );
        }
        while((gain !='N') && (gain !='n')&&(gain !='Y') &&
        (gain !='y'))
        printf("Is Above Information Correct? (y, n or ESC to
        quit) \n");
        c = getch( );
    }
    while((c == 'N') || (c == 'n') || (c == 0x0d));
    if (c == 0xib)
        exit(1);
    if ((fptr = fopen("c:\\qc25\\bin\\car.dat","r+b")) != NULL)
    {
        fread(dbuf,1,1024,fptr);
        topblk = 256*dbuf[0] + dbuf[1];
        if ((rec_num*24) > topblk)
        {
            printf("Record Out of Range!\n");
            fclose(fptr);
            exit(1);
        }
        fseek(fptr,((rec_num-1L)*24576L+1024L),SEEK_SET);
        if ((gain == 'Y')||(gain == 'y'))
        {
            printf("60 dB Ultrasound records extracted \n");
            for (i=0;i<6;i++)
            {
                fread(usrecord[i],1,2048,fptr);
                fread(dbuf,1,2048,fptr);
            }
        }
```

Appendix 1-continued
DATA ANALYSIS PROGRAM LISTING

```
            else
            {
                printf("40 dB Ultrasound records extracted \n");
                for (i=0;i<6;i++)
                {
                    fread(dbuf,1,2048,fptr);
                    fread(usrecord[i],1,2048,fptr);
                }
            }
        fclose(fptr);
        printf("Press any key to continue.\n");
        while((c=getch( ))==0x00);
        i=0;
        while (i<6)
        {
            _clearscreen(_GCLEARSCREEN);
            _settextposition(1,1);
            printf("Record -> %u \n",rec_num);
            printf("Transducer -> %u \n",i+1);
            _moveto(0,350);
            _lineto(639,350);
            _moveto(0,350);
            _lineto(0,370);
            _moveto(0,350-usrecord[i][0]);
            for(x=0;x<1280;x+=2)
            {
                _lineto(x/2, 350-usrecord[i][x]);
            }
            sptr=0;
            x=0;
            z=i;
            while ((sptr != 0x0d)&&(z == i))
            {
                _settextposition(40,1);
                print("                    ");
                _settextposition(40,1);
                printf("X Pointer at %d",x);
                sptr=getch( );
                switch(sptr)
                {
                    case 'f':
                    {
                        i++;
                        if (i==6)
                            i=5;
                        break;
                    }
                    case 'b':
                    {
                        i--;
                        if (i==-1)
                            i=0;
                        break;
                    }
                    case 77:
                    {
                        _setcolor(0);
                        _moveto(x/2,351);
                        _lineto(x/2,370);
                        if ((x+2)<1280)
                            x+=2;
                        _setcolor(1);
                        _moveto(x/2,351);
                        _lineto(x/2,370);
                        break;
                    }
                    case 75:
                    {
                        _setcolor(0);
                        _move(x/2,351);
                        _lineto(x/2,370);
                        if ((x-2)>0)
                            x-=2;
                        _setcolor(1);
                        _moveto(x/2,351);
                        _lineto(x/2,370);
                        break;
                    }
```

Appendix 1-continued
DATA ANALYSIS PROGRAM LISTING

```
                    }
                    case 54:
                    {
                        _setcolor(0);
                        _moveto(x/2,351);
                        _lineto(x/2,370);
                        if ((x+50)<1280)
                            x+=50;
                        _setcolor(1);
                        _moveto(x/2,351);
                        _lineto(x/2,370);
                        break;
                    }
                    case 52:
                    {
                        _setcolor(0);
                        _moveto(x/2,351);
                        _lineto(x/2,370);
                        if ((x-50)>0)
                            x-=50;
                        _setcolor(1):
                        _moveto(x/2,351);
                        _lineto(x/2,370);
                        break;
                    }
                    case 13:
                    {
                        i+=1;
                        sreg[i]=x;
                        break;
                    }
                }
            }
        }
        for (i=0;i<6;i++)
        {
            sum[i]=0;
            for(j=sreg[i];j<sreg[i]+800;j++)
                sum[i] = sum[i] + abs(usrecord[i][j]-119);
        }
        sum123 =(sum[0]+sum[1]+sum[2])/3;
        sum456 =(sum[3]+sum[4]+sum[5])/3;
        sum1to6 = (sum[0]+sum[1]+sum[2]+sum[3]+sum[4]+
            sum[5])/6;
        _clearscreen(_GCLEARSCREEN);
        printf("Transducers (1,2,3) Average Energy -> %u \n",
            sum123);
        printf("Transducers (4,5,6) Average Energy -> %u \n",
            sum456);
        printf("Transducers (1 to 6) Average Energy -> %u \n",
            sum1to6);
        while((c=getch( )==0x00);
    }
    else
    {
        _clearscreen(_GCLEARSCREEN);
        exit(1);
    }
}
```

We claim:

1. A portable apparatus for tissue characterization in live animals and/or animal carcasses comprising:
   a power source;
   a hand-held ultrasound transducer array; and
   a hand-held data acquisition unit operably coupled to the hand-held ultrasound transducer array and power source, the data acquisition unit including:
      data receiving means for receiving data from the transducer array;
      data input means for inputting data relevant to controlling the apparatus;
      data storage means for storing the ultrasound transducer array data and inputted data;

display means for displaying the transducer data and inputted data;

data export means for transferring data gathered from the transducer array; and data processing means for conditioning and analyzing data gathered from the transducer array and for providing an energy index representative of the tissue characteristics of the live animals or carcasses.

2. The apparatus of claim 1 wherein the power source is direct current.

3. The apparatus of claim 1 wherein the power source is alternating current.

4. The apparatus of claim 1 wherein the ultrasound transducer array is coupled to the data acquisition unit by cable.

5. The apparatus of claim 1 wherein the transducer is coupled to the data acquisition unit by wireless means for coupling.

6. In tissue characterization in live animals and/or animal carcasses using a piezo-electric transducer having a matching surface in association with a tissue surface of an animal to be analyzed, the improvement comprising a method of processing of a reflected signal from the tissue surface including the steps of:

processing said signal in a first mode to ascertain that acceptable contact and position have been made between the tissue surface of the animal and the matching surface of the piezo-electric transducer by analyzing the reflected signal from anatomical landmarks in the tissue on a quantitative as well as qualitative basis;

classifying the quality of the contact based on the energy level of the reflected signal and then processing said signal in a second mode to provide an energy index representative of tissue characteristics of the live animals or carcasses.

7. The method of claim 6 wherein the energy level of the reflected signal is measured by filtering, rectifying, and integrating the reflected signal.

8. The method of claim 6 wherein the energy level of the reflected signal is compared to a predetermined threshold power.

* * * * *